United States Patent [19]

Evans

[11] Patent Number: 5,129,946
[45] Date of Patent: Jul. 14, 1992

[54] COMPOSITIONS AND METHOD OF TREATMENT OF TIMBER

[75] Inventor: David L. Evans, Auckland, New Zealand

[73] Assignee: Hickson International PLc, West Yorkshire, United Kingdom

[21] Appl. No.: 652,317

[22] Filed: Feb. 7, 1991

Related U.S. Application Data

[63] Continuation of Ser. No. 187,296, Apr. 28, 1988, abandoned.

[30] Foreign Application Priority Data

Apr. 28, 1987 [NZ] New Zealand .................. 220130/87
Sep. 15, 1987 [NZ] New Zealand .................. 221810/87
Jan. 22, 1988 [NZ] New Zealand .................. 223277/88

[51] Int. Cl.$^5$ .............................................. B27K 3/52
[52] U.S. Cl. ................................. 106/18.3; 106/183; 106/213; 524/555; 524/380; 558/54
[58] Field of Search .............. 524/555, 380; 558/54; 106/18.3, 213, 183, 129

[56] References Cited

U.S. PATENT DOCUMENTS

| | | | |
|---|---|---|---|
| 1,926,253 | 9/1933 | Allen | 427/343 |
| 2,994,615 | 8/1961 | McDonald | 106/213 |
| 3,232,970 | 2/1966 | Hauptschein | 558/54 |
| 3,328,240 | 3/1966 | Hauptschein et al. | 558/54 |
| 3,767,439 | 10/1973 | Moyer et al. | 106/213 |
| 4,092,110 | 5/1978 | Adolphi et al. | 427/440 |
| 4,337,093 | 6/1982 | Metzner et al. | 106/18.35 |
| 4,461,721 | 7/1984 | Goettsche | 106/18.13 |
| 4,778,833 | 10/1988 | Van der Drift et al. | 524/404 X |
| 4,794,139 | 12/1988 | Braden et al. | 524/555 |

FOREIGN PATENT DOCUMENTS

| | | | |
|---|---|---|---|
| 8433827 | 10/1984 | Australia . | |
| 289317 | 2/1988 | European Pat. Off. | 106/18.3 |
| 205884 | 10/1983 | New Zealand . | |

OTHER PUBLICATIONS

Abstract AU 8433827-A Apr. 18 1985, Evans.

Primary Examiner—Karl Group
Attorney, Agent, or Firm—Birch, Stewart, Kolasch & Birch

[57] ABSTRACT

A composition for treating timber comprising a boron-containing preservative, a thickening agent and, optionally, a fluorosurfactant. The thickening agent can be at least one polysaccharide, such as xanthan gum, or two or more polyacrylamides. The boron-containing preservative can be in the form of a colloidal micro-crystalline suspension of a boron-containing salt. The composition allows the boron-containing preservative to be more readily absorbed by, and diffused into, the timber.

21 Claims, No Drawings 5,129,946

COMPOSITIONS AND METHOD OF TREATMENT OF TIMBER

This application is a continuation of application Ser. No. 07/187,296 filed on Apr. 28, 1988 now abandoned.

It is an object of this invention to provide compositions and methods for treating timber which go some way towards meeting the needs of the public and the industry.

BRIEF SUMMARY OF THE INVENTION

According to one aspect of this invention there is provided a composition for treating timber, including a boron-containing preservative, and a thickening agent, said thickening agent including one or more polysaccharides.

According to a further aspect of this invention there is provided a composition for treating timber, including a boron-containing preservative, and a thickening agent, said thickening agent including one or more polysaccharides, and one or more fluorosurfactants.

According to a further aspect of the present invention there is provided a composition for treating timber, including a boron-containing preservative; a thickening agent, wherein said thickening agent includes two or more polyacrylamides; and one or more fluorosurfactants.

According to a further aspect of this invention there is provided a composition for treating timber including boron salts in a micro-crystalline suspension, together with a thickening agent; wherein said thickening agent includes one or more polysaccharides.

According to a further aspect of this invention there is provided a composition for treating timber including boron salts in a micro-crystalline suspension, together with a thickening agent; wherein said thickening agent includes two or more polyacrylamides; and one or more fluorosurfactants.

According to a further aspect of this invention there is provided a composition for treating timber including a colloidal micro-crystalline suspension of boron-containing salts, together with a thickening agent in the form of one or more polysaccharides.

According to a further aspect of this invention there is provided a composition for treating timber including a colloidal micro-crystalline suspension of boron-containing salts, together with a thickening agent, in the form of two or more polyacrylamides, and one or more fluorosurfactants.

According to a further aspect of this invention there is provided a method of preparing a composition for treatment of timber including:
  i) heating water and adding thereto predetermined amounts of boric acid and borax;
  ii) stirring or agitating said solution;
  iii) cooling and stirring said solution; and
  iv) adding one or more polysaccharides.

According to a further aspect of this invention there is provided a method of preparing a composition for the treatment of timber including:
  i) heating water and adding thereto predetermined amounts of boric acid and borax;
  ii) stirring or agitating said solution;
  iii) cooling and stirring said solution; and
  iv) adding two or more polyacrylamides and one or more fluorosurfactants.

According to a further aspect of this invention there is provided a method of preparing a preservative composition for the treatment of timber including:
  i) heating from 7.4 to 29.5% (w/w) water;
  ii) adding thereto from 6.25 to 25% (w/w) boric acid and from 7.4 to 29.5% (w/w) borax;
  iii) stirring or agitating said solution;
  iv) cooling and stirring said solution;
  v) adding from 0.5 to 5.0% (w/w) polysaccharide; and
  vi) adding from 78.45 to 0% (w/w) water.

According to a further aspect of this invention there is provided a method of preparing a preservative composition for the treatment of timber including:
  i) heating from 7.4 to 29.5% (w/w) water;
  ii) adding thereto from 6.25 to 25% (w/w) boric acid and from 7.4 to 29.5% (w/w) borax;
  iii) stirring or agitating said solution;
  iv) cooling and stirring said solution;
  v) adding from 0.5 to 5.0% (w/w) polyacrylamide and up to 0.04% (w/w) fluorosurfactant;
  vi) adding from 78.45 to 0% (w/w) water.

According to a further aspect of this invention there is provided a method of treating timber which includes applying to said timber a preservative composition including a colloidal micro-crystalline suspension of boron-containing salts and a thickening agent including one or more polysaccharides; and allowing said composition to diffuse into said timber.

According to a further aspect of this invention there is provided a method of treating timber which includes applying to said timber a preservative composition including a colloidal micro-crystalline suspension of boron-containing salts, and a thickening agent including two or more polyacrylamides, and one or more fluorosurfactants; and allowing said composition to diffuse into said timber.

DETAILED DESCRIPTION OF THE PREFERRED EMBODIMENTS OF THE PRESENT INVENTION

The invention will now be described by way of example only and with reference to preferred embodiments thereof, although it should be appreciated that these are given by way of example only, and modifications and improvements may be made to the invention without departing from the scope thereof.

Compositions and methods of treating timber with a boron-containing preservative, wherein the preservative is applied to the timber as a solution or suspension of the boron-containing preservative together with a thickening agent, have previously been known and used. However, it has previously been found that in order to render preservative salts into a soluble state, substantial heating or mixing is necessary.

The present invention provides compositions and methods whereby the boron-containing salts are preferably held in a micro-crystalline suspension, in which state they have been found to be sufficiently and readily soluble. Normal crystals have often presented problems insofar as solubility and storage stability are concerned. By way of example, examination of micro-crystals of boron-containing salts of the present invention have shown that the size of such micro-crystals may be in the order of between approximately 10 to 30 microns, whereas the size of normal crystals of precipitated salts are found to be in the order from about 2 to 3 millimeters. This is however by way of example only, and compositions including crystals of larger size are also effective.

The micro-crystalline suspensions have been found to be relatively stable, with no tendency for precipitation of the preservative salts to occur, even on long standing. Thus, on the addition of water they are readily soluble and are able to be easily applied to and diffused into the timber.

A composition according to the present invention includes a thickening agent or polymers. Preferably, the thickening agent includes at least two polyacrylamides or at least one polysaccharide. Polyacrylamides and polysaccharides have been found to be particularly advantageous in use, however, it should be appreciated that other thickening agents may also be used. Examples include other water-soluble polymers.

By way of example, it has been found that polyacrylamides such as NALCATROL II (Registered Trade Mark), ALFLOC (Registered Trade Mark), or MAGNAFLOC (Registered Trade Mark) are particularly useful.

Also by way of example, it has been found that natural polysaccharides or polysaccharide containing compositions such as KELZAN (Trade Mark of Kelco) are useful. Another useful natural polysaccharide is RHODOPOL (Trade Mark of Rhone-Poulenc). An active ingredient of KELZAN is xanthan gum.

In the case of polyacrylamides, two or more suitable polyacrylamides are used to form the thickening agent. When polyacrylamides are used in a composition of the present invention, at least one fluorosurfactant is also added. In the case of polysaccharides, only one polysaccharide is generally used, and one or more fluorosurfactants may optionally be added to the composition.

Thus, it has been found that by adding into some compositions of the present invention one or more surface active agents in the form of fluorosurfactants, compositions of the present invention may exhibit increased properties which allow for an increase in surface wetting and diffusion rate.

It has also been found that by increasing the amount of thickening agent or polymer, with or without a fluorosurfactant, the resultant composition has increased properties of both solution uptake and diffusion rate.

The use of composition according to the present invention, including both the increased amount of thickening agent or polymer and with or without one or more fluorosurfactants, tends to decrease the surface energy of the composition and renders the composition into a state or form in which it is able to be more readily absorbed by and diffused into the timber.

Thus, compositions of the present invention, and methods of treating timber using such compositions allow for the boron-containing preservative salts to be more effectively and rapidly absorbed by diffusion into the timber.

One form of preparing a composition according to the present invention, and which is given by way of example only, firstly involves heating a predetermined amount of water, to a predetermined temperature. For example, the predetermined amount of water may be heated up to approximately 50° C.

Thereafter, a predetermined amount of borax is added and the mixture stirred. A predetermined amount of boric acid is then added. The mixture is preferably further stirred or agitated. If desired, following or immediately prior to the addition of the boric acid, the temperature may be increased. The addition of the borax and boric acid to the heated water, together with any stirring or agitation necessary, results in the borax and boric acid being dissolved into the water. Such stirring or agitation continues until such time as the borax and boric acid have fully dissolved into the solution.

Thereafter, the solution is cooled, preferably rapidly cooled to a predetermined temperature. For example, the solution may be cooled to approximately 20° C., or lower if desired.

The temperature to which the solution may be lowered depends to some extent on local climatic conditions. For example, 10° C. may be a more suitable temperature in Canada, Finland and the United Kingdom. Thereafter further stirring or agitation continues in order to prevent or minimise the formation of large crystals during re-crystallisation.

An appropriate thickening agent is then added. The thickening agent preferably includes two or more a polyacrylamides, or one or more polysaccharides.

One or more surfactants, such as for example a fluorosurfactant may then be added, in one preferred form of the invention. One or more fluorosurfactants are generally added when the thickening agent is includes polyacrylamides, and may optionally be added when the thickening agent includes one or more polysaccharides. This is, however, by way of example only, and it should be appreciated that the addition of a fluorosurfactant is not necessary in all forms of the invention.

An amount of water is then added, if necessary.

The resulting composition has a high viscosity and the boron-containing salts are held in a micro-crystalline suspension which is particularly suitable for transportation and storage. Further, given the micro-crystalline suspension of the boron-containing salts, the composition is able to be diluted in water in a straightforward manner, if necessary with the aid of stirring or pumping at ambient temperature, so as to result in a solution of a usable and acceptable concentration necessary to meet the appropriate solution strengths and viscosity for the application method used.

In one form of the invention, dilution of composition according to the present invention is made, such that the resulting composition includes a polysaccharide or polyacrylamide concentration of approximately 0.2% (w/w). This is by way of example only, however.

If desired, one or more additives such as fungicides and the like can be added, to further act upon and treat the timber and to stop fungal degradation during the subsequent diffusion period.

For example, the following are examples of antisapstain additives which may be used to:

sodium pentachlorophenoxide, captafol, copper-8 quinolinolate, TCMTB 2-(thiocyanomethylthio benzothiazole), methylene bisthiocyanate, TCMTB/methylene bisthiocyanate, carbendazim, IPBC (3-iodo-2-propynyl butyl carbamate), alkyl ammonium compounds and amine salts or mixtures of these, IPBC and one or more alkyl ammonium compounds, TCMTB and IPBC, carbendazim plus IPBC, sodium tetrachlorophenate, sodium tribromophenate, methylene bisthiocyanate and one or more alkylammonium compounds, TCMTB and one or more alkylammonium compounds, isothiazoline compounds e.g. n-octyl isothiazolin-2-one and mixtures containing these compounds, diiodomethyl-p-tolyl sulphone, diiodomethyl-p-tolyl-sulphone plus one or more alkyl ammonium compounds, inorganic fluorides e.g. potassium fluoride, folpet, thiophanate methyl plus chlorothalonil and mixtures thereof.

The advantages of the present invention result from the addition of an agent or polymers. The addition of one or more fluorosurfactants, in some forms of the invention, may also provide advantages over previously known compositions.

The amount of thickening agent or polymer used may be substantially increased or decreased over that previously known and used, and this has been found to at least assist in imparting into a composition according to the present invention increased properties of solution uptake and diffusion rate.

By way of example, a composition formed by the method referred to hereinbefore, may be as follows:

| Boric Acid | From 2.500 to 25.000% (w/w) |
| Borax | From 2.954 to 29.500% (w/w) |
| Water | From 4.335 to 43.356% (w/w) |
| Polymer | From 0.2 to 3.0% (w/w) |
| Fluorosurfactant | Up to 0.040% (w/w) |
| Fungicide (stain/mould inhibitor) | From 0.02 to 2.0% (w/w) |
| Water | Up to 90.02% (w/w) |

The following are specific examples of a composition according to the present invention:

EXAMPLE 1

The composition contains:

| Boric Acid | From 18.75% (w/w) |
| Borax (H2O) | From 22.14% (w/w) |
| Water | From 34.11% (w/w) |
| Nalcatrol II (80% Kerosene) | 1.3% (w/w) |
| Magnafloc E24 | 0.5% (w/w) |
| Water | 23.11% (w.w) |
| Methanol | 0.1% (w.w) |

The composition is formed using the following procedure:
1. Water is heated to 50° C. and borax is added and agitated. The temperature is increased to approximately 60° C. and boric acid is added. Further heating may be required (to approximately 65°-70° C.) until the solution is clear (water white). The solution is then crash-cooled to 25° C., with continuous agitation. '2. The thickener, NALCATROL II (80% dispersion in kerosene) is then added to the boron salt solution as it crystallises. In a separate vessel MAGNAFLOC E24, methanol and water are combined then mixed into the boron salt solution.
3. The antiapstain formulation is then added to the thickened composition.

EXAMPLE 2

A further formulation is as for Example 1, but substitutes NALCATROL II with 1.0% ALFLOC 622, a different polyacrylamide. The fluorosurfactant used is 0.003% Zonyl FSM 100. The differences in percentages from the above example are made up with water.

EXAMPLE 3

The composition contains:

| Boric Acid | 18.75% (w.w) |
| Borax | 22.50% (w/w) |
| Kelzan S | 0.5% (w/w) |
| Methanol | 0.5% (w/w) |
| Zonyl FSN 100 | 0.003% (w/w) |
| Water | 57.49% (w/w) |
| Antisapstain additive | 0.257% (w/w) |

The composition of this example is formed using substantially the same method as described in Example 1, with the polysaccharide being pre-swelled and mixed in with the methanol. The fluorosurfactant is then added to the slurry formed by the polysaccharide and the methanol, and the whole composition is added to the boron salt composition.

While the preferred thickening agent or polymer is a polyacrylamide or polysaccharide, is should be appreciated that other thickening agents may be used to advantage. For example, high molecular weight water-soluble polymers, including polyethylene oxides, acrylic emulsions and acrylic emulsion copolymers, and methyl vinyl ethers, along with proprietory formulations such as NALCATROL, (Trade Mark of Nalco Inc.), CARBOPOL (Trade Mark of B. F. Goodrich Company), FINNIFIX (Trade Mark of Metsaliitron Teollisuus Oy), MAGNAFLOC (Trade Mark of Allied Colloids) KELZAN (Trade Mark of Kelco), and RHODOPOL (Trade Mark of Rhone-Poulenc).

Referring now to preferred surfactants, it has been found that fluorosurfactants are particularly advantageous in some compositions and methods of the present invention, in that the addition of such fluorosurfactants has been found in some compositions to aid in surface wetting and to decrease surface energy. This allows for the composition and thus boron-containing salts to be more readily and effectively absorbed by and diffused by the timber, in some cases.

It has been found therefore that the addition of one or more fluorosurfactants at least assists in increasing the rate of diffusion, in some cases.

It has been found desirable to use fluorosurfactants having the general formulae:

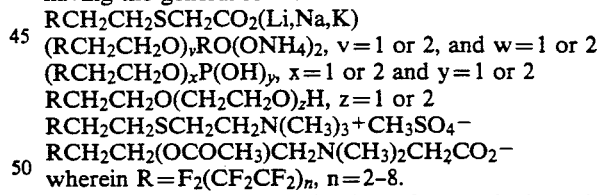

wherein $R = F_2(CF_2CF_2)_n$, $n = 2-8$.

Generic terms defining suitable surfactants include the following:
ammonium potassium or amine per fluoroalkyl sulphonates;
ammonium potassium or sodium fluorinated alkyl carboxylates;
fluorinated alkyl quaternary ammonium iodides;
fluorinated alkyl polyoxyethylene ethanols; and
fluorinated alkyl alcohoxylates, ethers or esters.

By way of example, and in one form of the invention, it is particularly advantageous to use a fluorosurfactant selected from the group known as ZONYLSs (Registered Trade Mark), having the formula:

wherein $m = 1-8$ and $n = 2-8$, and particularly having the formula $F(CF_2CF_2)_3CH_2CH_2O(CH_2CH_2O)_6H$, The above are by way of example only and it should be appreciated that fluorosurfactants of other formulae can be used. For example FLUORADs (Registered Trade Mark), may be used successfully.

In another preferred form of the invention organic phosphate surfactants may be used.

In some forms of the present invention, a suitable solvent may be used, which acts as a dispersion agent for the thickening agent. In some forms of the invention, a solvent such as methanol is added, while in other forms of the invention a suitable solvent is included in the proprietory formulations of the thickening agents used, and thus extra solvent need not be added. It should be appreciated, however, that the inclusion of a solvent is preferable, but not essential to the invention.

In order to render the composition of the present invention into a usable commercial state, desired or predetermined amounts of water can be added and the diluted composition then applied to the timber so that the diluted composition and boron-containing macro-crystalline salts may be diffused into the timber for the treating of the timber.

For example, compositions according to the present invention may comprise:
from 2.5 to 25.0% (w/w) boric acid;
from 2.954 to 29.500% (w/w) borax;
from 42.46 to 94.346% (w/w) water;
from 0.25 to 3.0% (w/w) polyacrylamide; and
up to 0.04% fluorosurfactant.

Another example of a composition according to the present invention comprises:
from 2.5 to 25.0% (w/w) boric acid;
from 2.954 to 29.500% (w/w) borax;
from 42.5 to 94.345% (w/w) water; and
from 0.25 to 3.0% (w/w) polysaccharide.

The present invention has been found to provide most satisfactory rates of absorption and diffusion.

This invention has been described by way of example only and improvements and modifications may be made without departing from the scope thereof, as defined in the appended claims.

We claim:

1. A composition for the treatment of timber comprising:
from 2.5 to 25.0% (w/w) boric acid;
from 2.954 to 29.500% (w/w) borax;
from 42.5 to 94.345% (w.w) water; and
from 0.25 to 3.0% (w.w) xanthan gum.

2. A composition for the treatment of timber, as claimed in claim 1, wherein said composition is diluted with water, before use.

3. A composition for treatment of timber, which comprises a boron-containing preservative and xanthan gum; wherein said composition is diluted with water.

4. A composition is claimed in claim 3, including at least one fluorosurfactant.

5. A method of treating timber which comprises applying to said timber a preservative composition which comprises boron-containing preservative and xanthan gum.

6. A method as claimed in claim 5, wherein said composition includes at least one fluorosurfactant.

7. A method of preparing a composition for the treatment of timber including i) heating water and adding thereto boric acid and borax;
ii) stirring or agitating said solution;
iii) cooling and stirring said solution;
iv) adding xanthan gum; and a fungicide.

8. A method is claimed in claim 7, including adding at least one fluorosurfactant.

9. A method of preparing a preservative composition for the treatment of timber comprising
i) heating from 7.4 to 28.5% (w/w) water;
ii) adding thereto from 6.25 to 25% (w/w) boric acid and from 7.4 to 29.5% (w/w) borax;
iii) stirring or agitating said solution;
iv) cooling and stirring said solution;
v) adding from 0.5 to 5.0% (w/w) xanthan gum;
vi) adding from 78.45 to 0% (w/w) water.

10. A composition for treating timber, wherein said composition comprises:

| | |
|---|---|
| Boric Acid | From 2.500 to 25.000% (w/w) |
| Borax | From 2.954 to 29.500% (w/w) |
| Water | From 4.335 to 92.6% (w/w) |
| Xanthan gum | From 1.950 to 2.064% (w/w) |
| Fluoro Surfactant | Up to 0.040% (w/w) |
| Water | |

11. A composition for treating timber comprising:

| | |
|---|---|
| Boric Acid | From 2.500 to 25.000% (w/w) |
| Borax | From 2.954 to 29.500% (w/w) |
| Water | From 4.335 to 94.355 (w/w) |
| Xanthum gum | From 0.2 to 3.0% (w/w) |
| Fluorosurfactant | Up to 0.040% (w/w) |
| Fungicide | From 0.02 to 2.0% (w/w) |

12. A composition for treating timber, which comprises a boron-containing preservative; and a xanthan gum.

13. A composition for treating timber, which comprises a boron-containing preservative; and a thickening agent consisting of a xanthan gum and at least one fluorosurfactant.

14. A composition for treating timber, which comprises a colloidal micro-crystalline suspension of a boron-containing salt; and a xanthan gum.

15. The composition according to claim 14, further comprising at least one fluorosurfactant.

16. A composition as claimed in any one of the claims 13 or 15 wherein said one and more fluorosurfactants is selected from the group consisting of:
$RCH_2CH_2SCH_2CO_2(Li,Na,K)$;
$(RCH_2CH_2O)_vRO(ONH_4)_2$, $v=1$ or 2, and $w=1$ or 2;
$(RCH_{2l}CH_2O)_xP(OH)_y$, $x=1$ or 2, and $y=1$ or 2;
$RCH_2CH_2O(CH_2CH_2O)_zH$, $z=1$ or 2;
$RCH_2CH_2SCH_2CH_2N(CH_3)_3{}^+CH_3SO_4{}^-$; or
$RCH_2CH_2(OCOCH_3)CH_2N(CH_3)_2CH_2CO_2{}^-$;
wherein $R=F_2(CF_2CF_2)_n$, $n=2-8$.

17. A composition as claimed in any one of claims 13 or 15 wherein said one or more fluorosurfactants is selected from the group consisting of:
ammonium potassium or amine per fluoroalkyl sulphonates;
ammonium potassium or sodium fluorinated alkyl carboxylates;
fluorinated alkyl quaternary ammonium iodides;
fluorinated alkyl polyoxyethylene ethanols, and
fluorinated alkyl alcohoxylates, ethers or esters.

18. A composition as claimed in any one of claims 13 or 15 wherein at least one of said fluorosurfactants is selected from the group of compounds, having the formula $F(CF_2CF_2)_m CH_2CH_2O (CH_2CH_2O)_n H$, wherein $m=2-8$ and $n=2-8$.

19. A composition as claimed in any one of claims 13 or 15 wherein at least one of said one or more fluorosurfactants is $F(CF_2CF_2)_3 CH_2CH_2O (CH_2CH_2O)_6 H$.

20. The composition according to any one of claims 12, 13 or 14 further comprising a fungicide.

21. A composition as claimed in claim 20, wherein said fungicide is selected from the group consisting of sodium pentachlorophenoxide, captafol, copper-8 quinolinolate, 2-(thiocyanomethylthio benzothiazole), methylene bisthiocyanate, 2-(thiocyanmomethylthio benzothiazole)/methylene bisthiocyanate, carbendazim, 3-iodo-2-propynyl butyl carbamate, alkyl ammonium compounds and amine salts or mixtures of these, 3-iodo-2-propynyl butyl carbamate and one or more alkyl ammonium compounds, 2-(thiocyanomethylthio benzothiazole) and 3-iodo-2-propynyl butyl carbamate, carbendazim plus 3-iodo-2-propynyl butyl carbamate, sodium tetrachlorophenate, sodium tribromophenate, methylene bisthiocyanate and one or more alkylammonium compounds, 2-(thiocyanomethylthio benzothiazole) and one or more alkylammonium compounds, isothiazoline compounds or mixtures thereof, including n-octyl isothiazolin-2-one, diiodomethyl-p-tolyl sulphone, diiodomethyl-p-tolyl-sulphone plus one or more alkyl ammonium compounds, inorganic fluorides including potassium fluoride, folpet, and thiophanate methyl plus chlorothalonil.

* * * * *